(12) United States Patent
Anderson et al.

(10) Patent No.: US 7,110,812 B1
(45) Date of Patent: Sep. 19, 2006

(54) CARDIAC DEFIBRILLATION

(75) Inventors: John McCune Anderson, Down (GB); Noel Evans, Magherafelt (GB)

(73) Assignee: UUTech Limited, (GB)

( * ) Notice: Subject to any disclaimer, the term of this patent is extended or adjusted under 35 U.S.C. 154(b) by 0 days.

(21) Appl. No.: 09/980,971

(22) PCT Filed: May 5, 2000

(86) PCT No.: PCT/GB00/01725

§ 371 (c)(1),
(2), (4) Date: Apr. 12, 2002

(87) PCT Pub. No.: WO00/67843

PCT Pub. Date: Nov. 16, 2000

(30) Foreign Application Priority Data

May 6, 1999 (GB) .................. 9910323.6

(51) Int. Cl.
*A61N 1/18* (2006.01)

(52) U.S. Cl. .......................................... 607/5

(58) Field of Classification Search .............. 607/3–34, 607/45, 59–61; 128/899, 903, 904
See application file for complete search history.

(56) References Cited

U.S. PATENT DOCUMENTS

| | | | |
|---|---|---|---|
| 3,796,221 A | 3/1974 | Hagfors | |
| 4,549,547 A | 10/1985 | Brighton et al. | |
| 5,411,537 A | 5/1995 | Munshi et al. | |
| 5,630,836 A * | 5/1997 | Prem et al. ................... | 607/61 |
| 5,697,958 A * | 12/1997 | Paul et al. ..................... | 607/31 |
| 5,735,887 A | 4/1998 | Barreras, Sr. et al. | |
| 6,016,449 A * | 1/2000 | Fischell et al. ............... | 607/45 |
| 6,321,117 B1 * | 11/2001 | Koshiol et al. ............... | 607/59 |

\* cited by examiner

*Primary Examiner*—George Manuel
(74) *Attorney, Agent, or Firm*—Kirkpatrick & Lockhart Nicholson Graham, LLP

(57) ABSTRACT

A defibrillator connected by catheters (7) to the heart (6) has an external circuit (2, 12) connected to a passive implanted circuit (5) by transdermal induction via voils (3, 4). For atrial defibrillation, pulses of 3–4 J can be transmitted at about 7 MHz without damage, using an implanted coil (4) of 20 mm diameter.

12 Claims, 3 Drawing Sheets

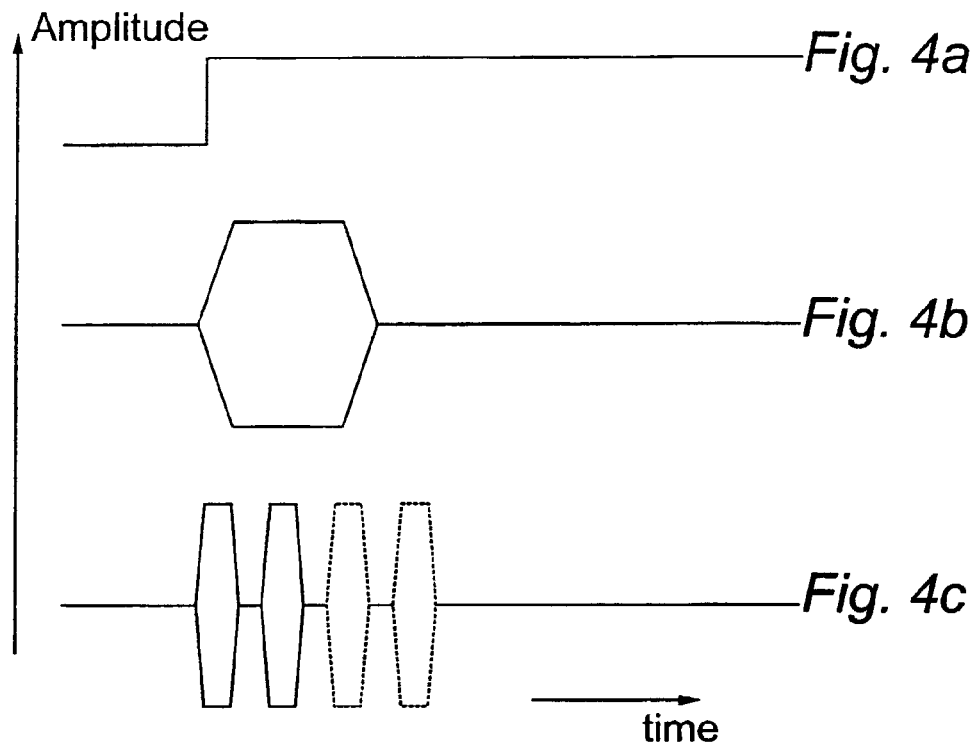
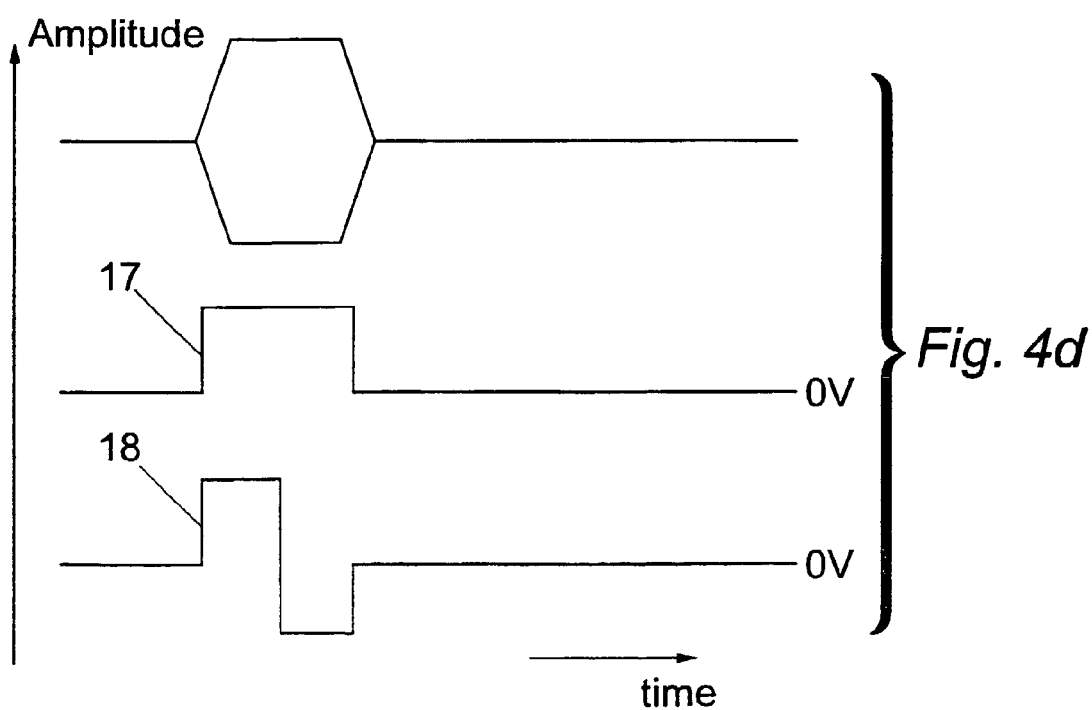

CARDIAC DEFIBRILLATION

This invention relates to cardiac defibrillation, and in particular (but not exclusively) to an apparatus for delivering an electrical defibrillating signal to a human heart in the state of atrial fibrillation (AF), using transdermal energy transfer to a passive implanted device.

Atrial fibrillation is a common heart arrhythmia that increases in prevalence with age, with typically 10% of people over the age of 70 experiencing an incident. The process of cardioversion of AF to normal sinus rhythm (SR) has traditionally been attempted by pharmacological measures or transthoracic direct current shock. The former has been limited by variable cardioversion rates and the risk of side effects, in particular proarrhythmia. The latter requires sedation or anaesthesia and high energy shocks, and there is a high recurrence rate. For these reasons, there has been interest in catheter-based transvenous atrial defibrillation and its potential use in an implantable atrial defibrillator. However, atrial implantable defibrillators are complex devices requiring on-board pattern recognition with complex recording and follow-up procedures. The need for electrical charging circuitry using active devices adds to the complexity and weight of the implant.

The present invention provides an apparatus for cardiac defibrillation which comprises an external circuit and an implantable circuit; the external circuit including an induction transmitting coil and signal generating means for applying radio frequency pulses of predetermined shape to the transmitting coil; the implantable circuit including an induction receiving coil for receiving pulses when the two coils are in proximity, and a rectification circuit having an input connected to the receiving coil and an output driving electrodes implantable in the heart.

In a preferred form of the invention, for use in atrial defibrillation, the power transmitted per pulse is less than about 5 J and the radio frequency is in the range 3–30 MHz, typically about 7 MHz.

Most preferably, the implantable circuit contains only passive components.

From another aspect the invention provides a method of cardiac (preferably atrial) defibrillation which comprises transmitting pulses of controlled shape and energy transdermally by high frequency magnetic induction to a substantially passive implanted circuit which includes electrodes implanted in the heart.

It is known to transfer energy transdermally by induction, but only for purposes of recharging batteries in implanted devices such as pacemakers or continuously powering implanted devices such as pumps. It has not hitherto been proposed to use such techniques to transfer controlled waveforms for high energy physiological stimulation.

An embodiment of the invention will now be described, by way of example, with reference to the accompanying drawings, in which:

FIG. 4 illustrates waveforms in the apparatus.

Figure 1:
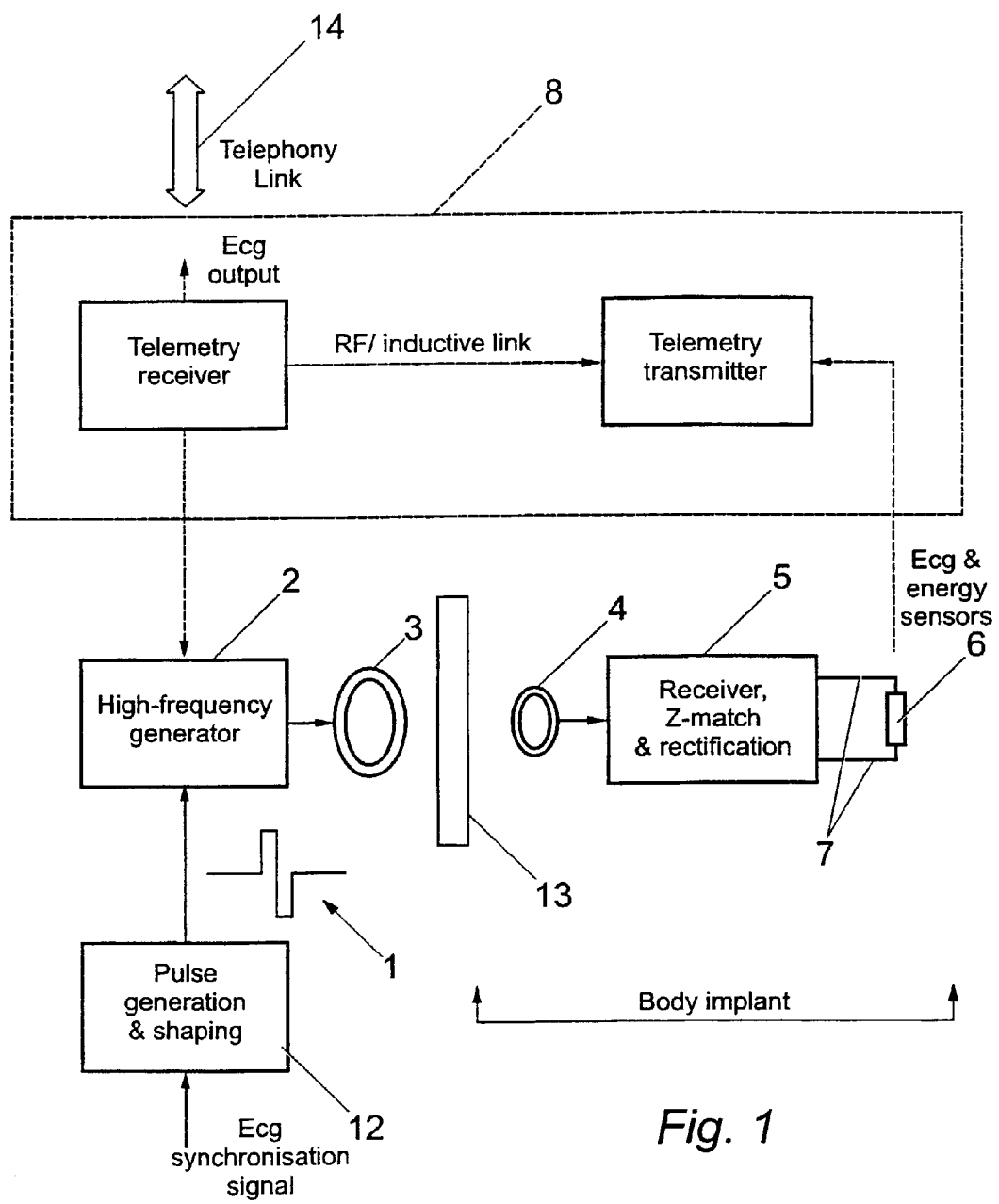
FIG. 1 shows the elements required for controlled, transdermal energy delivery to a cardiac load.

In the apparatus (FIG. 1), an appropriately synchronised trigger pulse is firstly generated, based on the subject's electrocardiogram (ecg). This pulse, after shaping in a pulse generation and shaping circuit 12 to a waveform 1 suitable for AF conversion, is used to amplitude modulate a radio frequency (RF) carrier generator 2 at a power level consistent with the transmission of 1–5 J of energy to the internal load, itself nominally 50Ω resistive. The transmission path takes the form of a pair of coaxially-aligned transmit 3 and receive 4 inductors constructed in the form of an RF transformer. The diameters of the coils 3 and 4 are set so as to optimise energy transfer at a physical spacing not less than the thickness of the thoracic wall 13. Both inductors are wound with enamelled copper wire. The transmitting coil 3 is mounted on an insulated paddle to facilitate adjustment in its placement on the subject's body. The implanted circuitry is mounted on a printed circuit board and consists of the receiving coil 4 connected to impedance matching, rectification and wave-shaping components 5. The final defibrillating signal is connected to the heart (indicated as an electrical load 6) by catheters 7, one placed in the lateral right atrium (RA) and the other in the distal great cardiac vein via the coronary sinus. Alternatively, any conventional atrial defibrillation delivery system may be used.

In one example, the coils 3 and 4 are designed to give optimum inductive coupling at a centre-to-centre spacing of 20 mm. Given a maximum diameter, for practicability, of the receiving coil 4 of 35 mm, the transmitting coil 3 has a diameter of 53 mm. Both inductors are wound with 1.5 mm enamelled copper wire. The transmitting coil 3 is arranged as a solenoidal coil, spaced at one turn. The receiving coil 4 is pile-wound to conserve space in the final implant.

Figure 2:
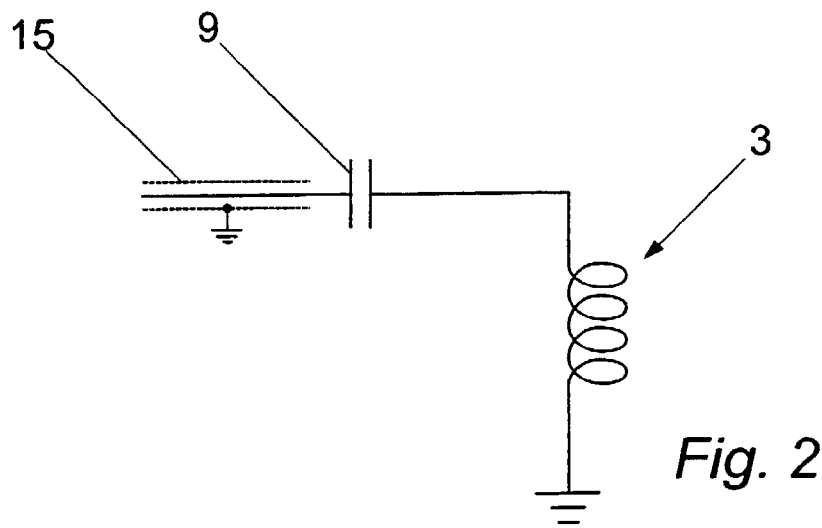
FIG. 2 illustrates the circuitry required external to the body.
Figure 3:
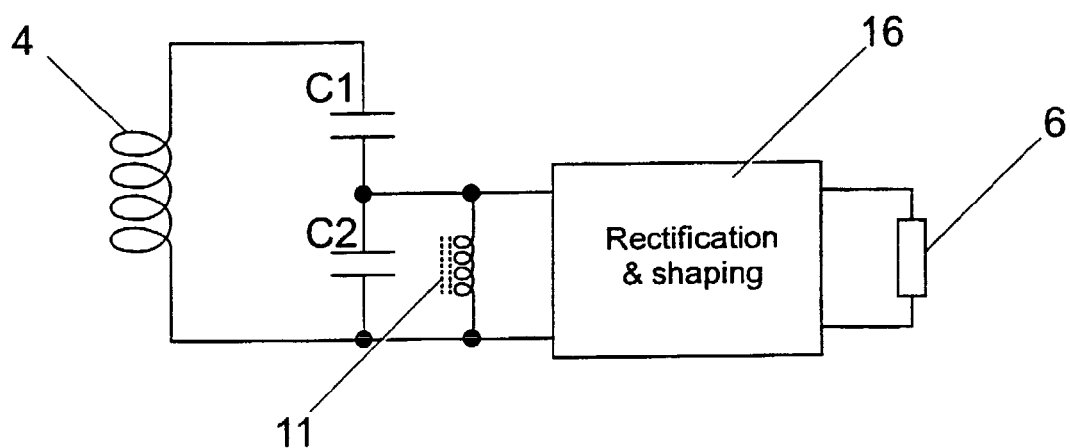
FIG. 3 represents the body-internal circuitry.

Both inductors in the apparatus are tuned to resonance at the selected operating frequency of the system, typically in the range 3–30 MHz. As seen in FIG. 2, the transmitter uses series tuning by capacitor 9. FIG. 2 also shows a 50 ohm feed 15 from the generator 2, giving an operational loaded Q of approximately 5. Referring to FIG. 3, the receiving coil is parallel tuned, with capacitive matching to the load 6 by means of capacitors C1 and C2. A radio-frequency choke 11 provides a DC path for rectifier current. Rectification and shaping is effected in circuit 16.

Optionally, as shown in FIG. 1 a telemetry link 8 may be incorporated to provide ecg monitoring and feedback-derived, automatic tuning of the energy delivery system. Such a link may also be powered from energy delivered transdermally, by using a low-power transfer to power up the telemetry link, or to charge an on-board battery. Alternatively, the ecg could be transmitted via the induction coils using a suspended carrier technique.

As is also indicated in FIG. 1, the external circuitry may include a remote communication link 14, which may be via telephone communication (landline or GSM) or via a radio link. This would, for example, enable the patient's ecg to be transmitted to a hospital for monitoring and for inspection by a physician. Defibrillation could be activated remotely, and spoken instructions could be conveyed to the patient.

Atrial defibrillation currently requires a pulse energy of about 3 to 4 J. By using a tuned inductive coupling as described, typically at a frequency about 7 MHz, these energy levels can be transmitted transdermally while maintaining control of pulse shape and timing. It is contemplated that by refining the pulse shape, duration and timing required to achieve defibrillation the energy necessary could be reduced to 1 J or less, which would be painless to the patient and remove any need for sedation.

The pulse form 1 shown in FIG. 1 is a biphasic pulse, which is the form we currently prefer. However, other pulse forms and hence RF envelope shapes may also be used, such as monophasic and multiple. FIG. 4 illustrates waveforms of the apparatus in more detail. FIG. 4a is a typical trigger input from an ecg. FIG. 4b shows a typical RF output envelope to the coil 3 as a single pulse. FIG. 4c shows an alternative RF output envelope as a burst of two or more pulses. All pulses can be controlled in width, and the inter-pulse gap of FIG. 4c is programmable. Each RF pulse, after transmission and rectification, results in either a monophasic or a biphasic (baseband) voltage waveform suitable for driving the cardiac load. FIG. 4d shows a monophasic pulse 17 and a biphasic pulse 18 which can be produced from the single pulse of FIG. 4a.

Although described above with particular reference to atrial defibrillation, the invention could find use in ventricular defibrillation. Here, though, the required energy levels are much higher (typically about 15 J).

It will be appreciated that one of the benefits of the embodiment described is that the implanted hardware is entirely passive and does not require any implanted power source. However, the invention does not exclude the possibility of some active components being implanted, with a reduced requirement for an internal source of power.

What is claimed is:

1. An apparatus for cardiac defibrillation which comprises an external circuit and an implantable circuit; the external circuit including an induction transmitting coil and signal generating means for applying radio frequency pulses of predetermined shape to the transmitting coil; the radio frequency pulses having energy levels such as to cause defibrillation; the implantable circuit including an induction receiving coil for receiving the defibrillation radio frequency pulses when the two coils are in proximity, and a rectification circuit having an input connected to the receiving coil and an output driving electrodes implantable in the heart, to transfer defibrillation signals to the heart.

2. An apparatus according to claim 1, for use in atrial defibrillation, in which the power transmitted per pulse is less than about 5 J and the radio frequency is in the range 3–30 MHz.

3. The apparatus according to claim 2 wherein said radio frequency is about 7 MHZ.

4. An apparatus according to claim 1 or claim 2, in which the signal generating means comprises a radio frequency generator switched or gated under the control of a pulse generation and shaping means which in turn is responsive to an ecg synchronisation signal.

5. An apparatus according to claim 4, in which the ecg synchronisation signal is provided via a telemetry transmitter implanted in the patient.

6. An apparatus according to claim 1, in which the external circuit further includes a telephony link by which the ecg may be transmitted to, and/or the apparatus controlled from, a remote location.

7. An apparatus according claim 1, in which the external and implantable circuits include impedance matching components to achieve a high degree of tuning.

8. An apparatus according to claim 7, in which the inductive coupling is tuned to resonance.

9. An apparatus according to claim 8 in which the inductive coupling is tuned to resonance by use of series resonance in the external circuit and parallel resonance in the implantable circuit.

10. An apparatus according to claim 1, in which the implantable circuit contains only passive components.

11. A method of cardiac defibrillation which comprises transmitting pulses of controlled shape and energy transdermally by high frequency magnetic induction from an external circuit, which pulses have energy levels such as to cause defibrillation, to a substantially passive implanted circuit which receives the defibrillation pulses and includes electrodes implantable in the heart, to transfer the defibrillation pulses to the heart.

12. The method of claim 11, in which the electrodes are implanted to provide atrial defibrillation.

* * * * *

UNITED STATES PATENT AND TRADEMARK OFFICE
CERTIFICATE OF CORRECTION

| | | |
|---|---|---|
| PATENT NO. | : 7,110,812 B1 | Page 1 of 1 |
| APPLICATION NO. | : 09/980971 | |
| DATED | : September 19, 2006 | |
| INVENTOR(S) | : Anderson et al. | |

It is certified that error appears in the above-identified patent and that said Letters Patent is hereby corrected as shown below:

Column 4, Line 13, the phrase reading "An apparatus according claim 1" should read --An apparatus according to claim 1--.

Signed and Sealed this

Twelfth Day of December, 2006

JON W. DUDAS
*Director of the United States Patent and Trademark Office*